US010905817B2

(12) United States Patent
Ali et al.

(10) Patent No.: US 10,905,817 B2
(45) Date of Patent: Feb. 2, 2021

(54) SYSTEMS AND METHODS FOR MONITORING AND CONTROLLING FLUID BALANCE DURING A BIOLOGICAL FLUID PROCEDURE

(71) Applicant: Fenwal, Inc., Lake Zurich, IL (US)

(72) Inventors: Zahra R. Ali, Chicago, IL (US); Lan T. Nguyen, Vernon Hills, IL (US)

(73) Assignee: Fenwal, Inc., Lake Zurich, IL (US)

( * ) Notice: Subject to any disclaimer, the term of this patent is extended or adjusted under 35 U.S.C. 154(b) by 96 days.

(21) Appl. No.: 16/149,622

(22) Filed: Oct. 2, 2018

(65) Prior Publication Data

US 2019/0099541 A1   Apr. 4, 2019

Related U.S. Application Data

(60) Provisional application No. 62/567,081, filed on Oct. 2, 2017.

(51) Int. Cl.
*A61M 1/36* (2006.01)
*A61M 1/38* (2006.01)
*A61M 1/02* (2006.01)

(52) U.S. Cl.
CPC ........ *A61M 1/3607* (2014.02); *A61M 1/0209* (2013.01); *A61M 1/361* (2014.02);
(Continued)

(58) Field of Classification Search
CPC .. A61M 1/0209; A61M 1/3607; A61M 1/361; A61M 1/3643; A61M 1/3672; A61M 1/3683; A61M 1/3693; A61M 1/3696; A61M 1/38; A61M 2202/0092; A61M 2202/0407; A61M 2202/0413;
(Continued)

(56) References Cited

U.S. PATENT DOCUMENTS 5,360,542 A   11/1994  Williamson, IV et al.
5,868,696 A   2/1999   Giesler et al.
(Continued)

FOREIGN PATENT DOCUMENTS

EP   3132817 A1   2/2017

OTHER PUBLICATIONS

Peritt, D.. "Potential mechanisms of photopheresis in hematopoietic stem cell transplantation." Biology of blood and marrow transplantation : journal of the American Society for Blood and Marrow Transplantation 12 1 Suppl 2 (2006): 7-12.

*Primary Examiner* — Dirk R Bass
(74) *Attorney, Agent, or Firm* — Cook Alex Ltd.

(57) ABSTRACT

Described is a method for controlling fluid volume balance. A controller is configured with a first set of inputs comprising a hematocrit, a total blood volume, and an ACD ratio. A maximum extracorporeal RBC amount during the procedure is estimated based on the first set of inputs. A fluid circuit is primed with a priming fluid. Whole blood is drawn from a blood source and separated into a RBC component, a target cell component, and a plasma component. The target cell component is directed to a product container. The product container comprising the target cell component is treated. A treated target cell component, a portion of the RBC component remaining in the fluid circuit, and/or a portion of the plasma component remaining in the fluid circuit are returned to the blood source. A first response action is provided if the maximum extracorporeal RBC amount estimated is above a programmed limit.

20 Claims, 5 Drawing Sheets

(52) U.S. Cl.
CPC ........ *A61M 1/3643* (2013.01); *A61M 1/3672* (2013.01); *A61M 1/3683* (2014.02); *A61M 1/3693* (2013.01); *A61M 1/3696* (2014.02); *A61M 1/38* (2013.01); A61M 2202/0092 (2013.01); A61M 2202/0407 (2013.01); A61M 2202/0413 (2013.01); A61M 2202/0415 (2013.01); A61M 2202/0429 (2013.01); A61M 2202/0439 (2013.01); A61M 2202/0443 (2013.01); A61M 2205/3386 (2013.01); A61M 2205/50 (2013.01); A61M 2230/005 (2013.01); A61M 2230/207 (2013.01)

(58) Field of Classification Search
CPC .. A61M 2202/0415; A61M 2202/0429; A61M 2202/0439; A61M 2202/0443; A61M 2205/3386; A61M 2205/50; A61M 2230/005; A61M 2230/207
See application file for complete search history.

(56) References Cited

U.S. PATENT DOCUMENTS

| | | |
|---|---|---|
| 6,027,657 A | 2/2000 | Min et al. |
| 7,433,030 B2 | 10/2008 | Waldo et al. |
| 2013/0267884 A1 | 10/2013 | Boggs et al. |

SYSTEMS AND METHODS FOR MONITORING AND CONTROLLING FLUID BALANCE DURING A BIOLOGICAL FLUID PROCEDURE

CROSS-REFERENCE TO RELATED APPLICATIONS

This application claims the benefit of U.S. Provisional Patent App. No. 62/567,081 filed Oct. 2, 2017, which is expressly incorporated herein by reference in its entirety.

FIELD OF THE DISCLOSURE

The present disclosure relates generally to systems and methods for monitoring and controlling fluid balance in medical procedures and, in particular to systems and methods for monitoring and controlling fluid volumes in a blood processing procedure.

BACKGROUND

Whole blood is made up of various cellular and non-cellular components such as red cells, white cells and platelets suspended in its liquid component, plasma. Whole blood may be separated into its constituent components (cellular, liquid or other), and the separated component(s) may be administered to a patient in need of that particular component or components.

The administration of blood and/or blood components is common in the treatment of patients suffering from disease. Rather than infuse whole blood, individual components may be administered to the patient(s) as their needs require. For example, administration (infusion) of platelets may often be prescribed for cancer patients whose ability to make platelets has been compromised by chemotherapy. Infusion of white blood cells (i.e., mononuclear cells) after the cells have undergone some additional processing or treatment may also be prescribed for therapeutic reasons, including treatment of diseases that specifically involve the white blood cells. Thus, it may be desirable to separate and collect the desired blood component from whole blood and then treat the patient with the specific blood component. The remaining components may be returned to the patient or retained for other uses.

There are several diseases or disorders which are believed to primarily involve mononuclear cells, such as cutaneous T-cell lymphoma, organ allograft rejection after transplantation and autoimmune diseases such as rheumatoid arthritis and systemic sclerosis, among others.

Cutaneous T-cell lymphoma (CTCL) is a term that is used to describe a wide variety of disorders. Generally, CTCL is a type of cancer of the immune system where T-cells (a type of mononuclear cell) mutate or grow in an uncontrolled way, migrate to the skin and form itchy, scaly plaques or patches. More advanced stages of the disease also affect the lymph nodes. Therapeutic treatment options for CTCL have previously been limited. While chemotherapy has been utilized, this particular form of treatment also has many associated undesirable side effects, such as lowered resistance to infection, bleeding, bruising, nausea, infertility and hair loss, just to name a few.

Organ allograft rejection may be characterized as the rejection of tissues that are foreign to a host, including transplanted cardiac tissue as well as lung, liver and renal transplants. Immunosuppression drug therapy following transplantation is common. However, there are potential drawbacks including reoccurring infection due to the compromised competence of the immune system caused by this type of therapy.

Similarly, graft versus host disease (GVHD) is a complication that can occur after a stem cell or bone marrow transplant in which the newly transplanted material attacks the transplant recipient's body. The differences between the donor's cells and recipient's tissues often cause T-cells from the donor to recognize the recipient's body tissues as foreign, thereby causing the newly transplanted cells to attack the recipient. GVHD may complicate stem cell or bone marrow transplantation, thereby potentially limiting these life-saving therapies. Therefore, after a transplant, the recipient may be administered a drug that suppresses the immune system, which helps reduce the chances or severity of GVHD.

Autoimmune diseases, including rheumatoid arthritis (RA) and progressive systemic sclerosis (PSS), can be characterized by an overactive immune system which mistakes the body's own tissues as being a foreign substance. As a result, the body makes autoantibodies that attack normal cells and tissues. At the same time, regulatory T-cells, which normally function to regulate the immune system and suppress excessive reactions or autoimmunity, fail in this capacity. This may lead to among other things, joint destruction in RA and inflammation of the connective tissue in PSS.

SUMMARY

According to an exemplary embodiment, the present disclosure is directed to a system for monitoring and controlling fluid balance during an extracorporeal photopheresis procedure. The system comprises a disposable fluid circuit comprising a product container configured to receive a target cell component. The system also comprises a separator configured to work in association with the disposable fluid circuit, the separator comprising a chamber configured to rotate about a rotational axis and convey whole blood from a blood source into an inlet region of the chamber for separation into a red blood cell component, a plasma component, and the target cell component. The system also comprises a microprocessor-based controller in communication with the separator. The controller is configured to estimate an end-of-procedure fluid balance by calculating a total volume of anticoagulant solution having a citrate concentration to be used for the procedure, wherein the end-of-procedure fluid balance is estimated based on manual or automatic inputs comprising an ACD ratio relating unanticoagulated extracorporeal whole blood to anticoagulant solution, an amount of whole blood to process, a citrate infusion threshold rate, a patient body weight associated with the blood source, and a total blood volume of the blood source. The controller is also configured to draw anticoagulated whole blood into the disposable fluid circuit and the chamber at a whole blood flow rate. The controller is also configured to separate the anticoagulated whole blood into the red blood cell component, the target cell component, and the plasma component. The controller is also configured to direct the target cell component to the product container, treat the product container comprising the target cell component to create a treated target cell component, and return to the blood source the treated target cell component, a portion of the red blood cell component remaining in the fluid circuit, and/or a portion of the plasma component remaining in the fluid circuit. The controller is also configured to provide a first response action if the end-of-procedure fluid balance estimated is above or below a programmed fluid balance range.

According to an exemplary embodiment, the present disclosure is directed to a method for monitoring and controlling fluid volume balance during an extracorporeal photopheresis procedure, driven and adjusted by a microprocessor-based controller. The controller is configured manually or automatically with a first set of inputs comprising a hematocrit of a blood source, a total blood volume of the blood source, and an ACD ratio relating unanticoagulated extracorporeal whole blood to anticoagulant solution. A maximum extracorporeal red blood cell amount during the procedure is estimated based on the first set of inputs. A fluid circuit is primed with a priming fluid having a prime fluid hematocrit value inputted into the controller. Whole blood is drawn from the blood source into the fluid circuit and a separator. The whole blood is separated into a red blood cell component, a target cell component, and a plasma component. The target cell component is directed to a product container. The product container comprising the target cell component is treated to create a treated target cell component. The treated target cell component, a portion of the red blood cell component remaining in the fluid circuit, and/or a portion of the plasma component remaining in the fluid circuit is returned to the blood source. A first response action is provided if the maximum extracorporeal red blood cell amount estimated is above a programmed limit.

According to an exemplary embodiment, the present disclosure is directed to a method for monitoring and controlling fluid volume balance during an extracorporeal photopheresis procedure, driven and adjusted by a microprocessor-based controller. 1) The controller is configured manually or automatically with inputs comprising a hematocrit of a blood source, a total blood volume of the blood source, an ACD ratio relating unanticoagulated extracorporeal whole blood to anticoagulant solution, a citrate infusion threshold rate, a volume of whole blood to process, and a patient body weight associated with the blood source. 2) A fluid circuit is primed with a priming fluid. 3) None or some of the priming fluid is returned to the blood source. 4) Whole blood is withdrawn from the blood source into the fluid circuit at a first flow rate and anticoagulant solution is withdrawn at a second flow rate in accordance with the ACD ratio, the citrate infusion threshold rate, the volume of whole blood to process, and the patient body weight. 5) The whole blood is separated within a separation chamber into a red blood cell component, a mononuclear cell component, and a plasma component. 6) A first portion of the red blood cell component and a first portion of the plasma component are returned to the blood source. 7) A second portion of the red blood cell component and a second portion of the plasma component are retained within the fluid circuit. 8) The mononuclear cell component is collected in the separation chamber over a plurality of cycles comprising steps 4 through 7, while anticoagulated whole blood enters the separation chamber continuously, at select intervals, and/or for a predetermined period of time. 9) A volume of fluid comprising the mononuclear cell component and a third portion of the red blood cell component is pumped from the separation chamber at an MNC transfer rate. 10) The mononuclear cell component is directed into a first container without the red blood cell component. 11) The mononuclear cell component is diluted with a volume of the second portion of the plasma component within the fluid circuit pumped into the first container at a PRP rate. 12) A photoactivation agent is added to the mononuclear cell component to create an agent-added mononuclear cell component. 13) The agent-added mononuclear cell component is irradiated to create a photoactivated mononuclear cell component. 14) The photoactivated mononuclear cell component, the second portion of the red blood cell component, and/or the second portion of the plasma component is returned. The controller is configured to estimate throughout the procedure an end-of-procedure fluid balance based on the inputs of step 1, any priming fluid returned to the blood source in step 3, the volume of fluid in step 9, the MNC transfer rate in step 9, the volume of the second portion of the plasma component within the fluid circuit in step 11, and the PRP rate in step 11. The controller is configured to provide a response action if the end-of-procedure fluid balance is above or below a programmed fluid balance range.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Where existing therapies for treating one or more diseases may result in certain unintended side effects, additional treatment may be desired or required. One procedure which has been shown to be effective in the treatment of diseases and/or the side effects of existing therapies involving mononuclear cells is extracorporeal photopheresis or "ECP". Extracorporeal photopheresis (also sometimes referred to as extracorporeal photochemotherapy) is a process that may include: (1) collection of mononuclear cells (MNC) from a blood source (e.g., patient, donor, blood-filled bag, etc.), (2) photoactivation treatment of the collected MNC cells, and (3) re-infusion of the treated cells (MNC) back to the blood source. More specifically, ECP involves the extracorporeal exposure of peripheral blood mononuclear cells combined with a photoactive compound, such as 8-methoxypsoralen or "8-MOP" which is then photoactivated by ultraviolet light, followed by the re-infusion of the treated mononuclear cells.

The combination of 8-MOP and UV radiation may cause apoptosis or programmed cell death of ECP-treated T-cells.

During ECP treatment, photoactivation is known to cause 8-MOP to irreversibly covalently bind to the DNA strands contained in the T-cell nucleus. When the photochemically damaged T-cells are reinfused, cytotoxic effects are induced. For example, a cytotoxic T-cell or "CD8+ cell" releases cytotoxins when exposed to infected or damaged cells or otherwise attacks cells carrying certain foreign or abnormal molecules on their surfaces. The cytotoxins target the damaged cell's membrane and enter the target cell, which eventually leads to apoptosis or programmed cell death of the targeted cell. In other words, after the treated mononuclear cells are returned to the body, the immune system recognizes the dying abnormal cells and begins to produce healthy lymphocytes (T-cells) to fight against those cells.

ECP may result in an immune tolerant response in a patient. For example, in the case of graft versus-host disease, the infusion of apoptotic cells may stimulate regulatory T-cell generation, inhibit inflammatory cytokine production, cause the deletion of effective T-cells and result in other responses. See Peritt, "Potential Mechanisms of Photopheresis in Hematopoietic Stem Cell Transplantation," Biology of Blood and Marrow Transplantation 12:7-12 (2006).

Figure 1:
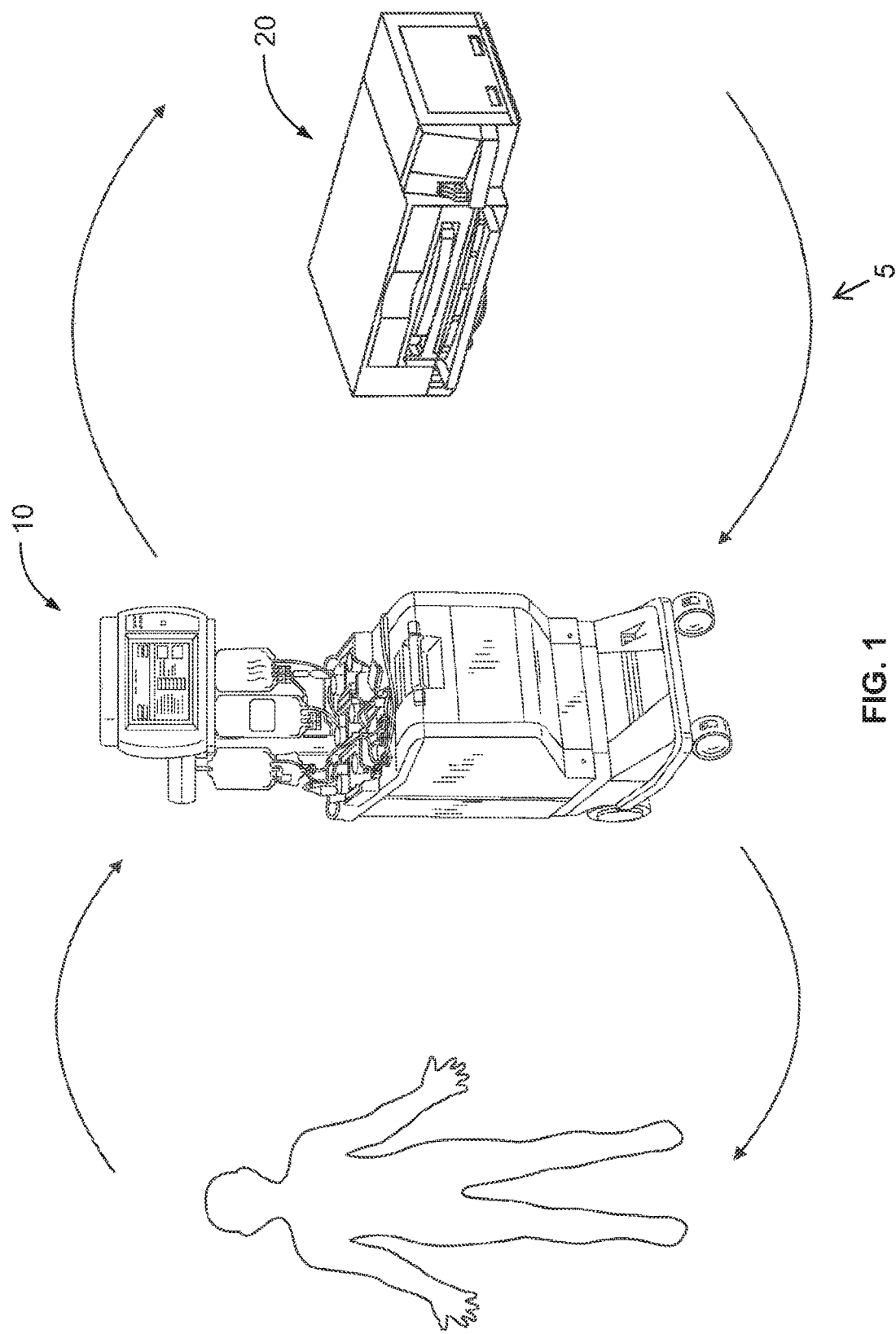
FIG. 1 is a diagram generally showing mechanical components of a photopheresis treatment device, according to an exemplary embodiment.
Figure 2:
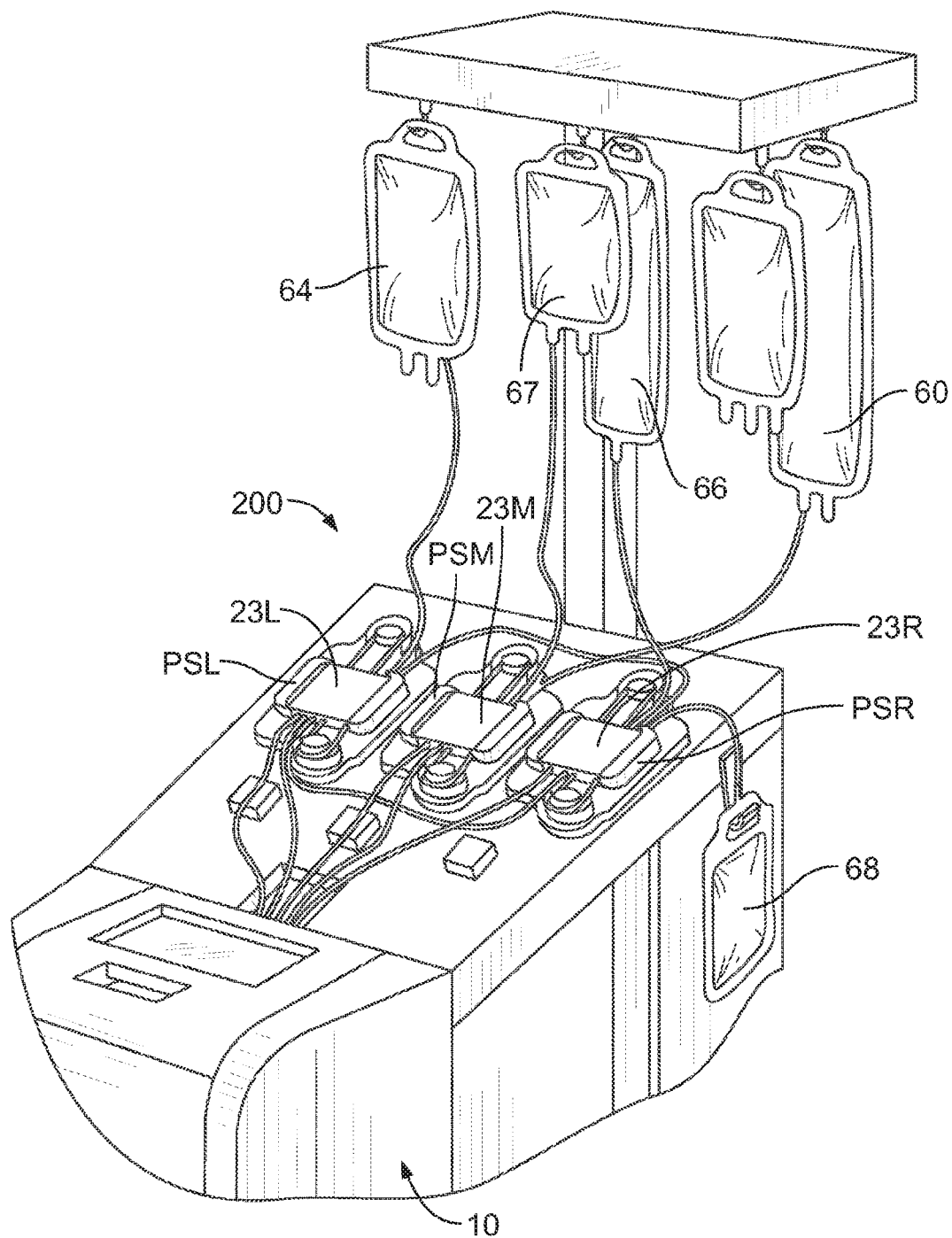
FIG. 2 is a partial perspective view of an apheresis separator useful in the methods and systems described herein, according to an exemplary embodiment.
Figure 4:
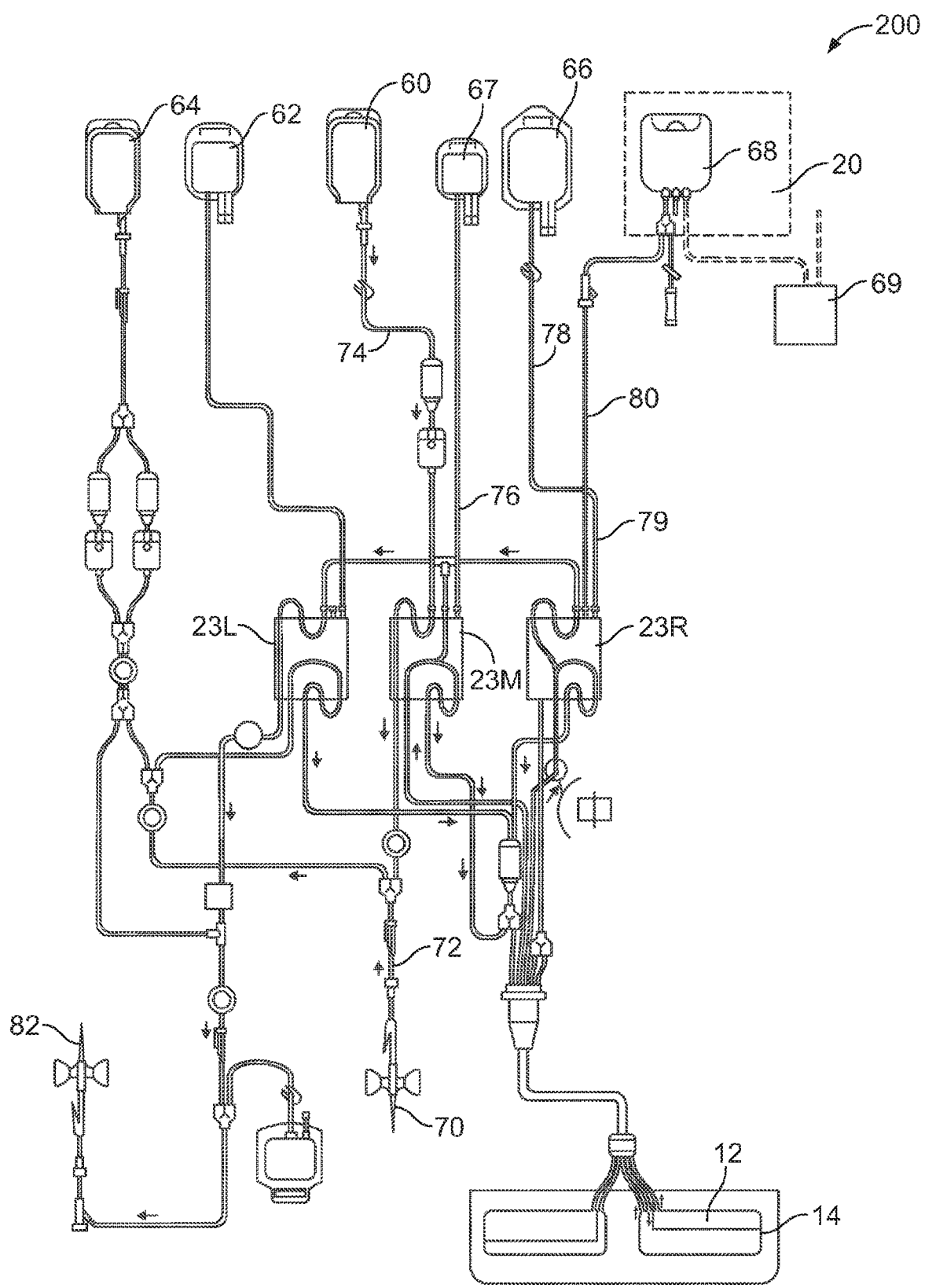
FIG. 4 is a diagram of a fluid circuit useful in the collection, treatment and reinfusion of target cells, according to an exemplary embodiment.

FIG. 1 shows, in general, the mechanical components that make up an ECP system 5 and that may be used in one or more of the systems and methods described herein. The system 5 may include a separation component 10 and a treatment (i.e., irradiation) component 20. Irradiation component 20 may be independent and housed separately from the separation component 10, or components 20 and 10 may be integrated into a single device. In an embodiment in which components 20 and 10 are housed separately, the separation device 10 and irradiation device 20 may be located adjacent to each other, allowing an operator or clinician to have access to both devices during a particular treatment procedure. A blood source may be connected to a fluid circuit 200 as shown in FIGS. 1, 2, 4 that provides a sterile closed pathway between separation component 10 and irradiation component 20 and may be cooperatively mounted on the hardware of the separation device 10. The separation device 10 may have one or more features of an apheresis device, such as a system marketed as the AMICUS® separator by Fenwal, Inc. of Lake Zurich, Ill., as described in greater detail in U.S. Pat. No. 5,868,696, which is hereby incorporated herein by reference in its entirety, although any suitable separation device may be used.

With reference to FIG. 1, whole blood may be withdrawn from the blood source and introduced into the separation component 10 where the whole blood is separated to provide a target cell population. In one embodiment, the target cell population may be mononuclear cells (MNCs) or MNCs of a particular type (lymphocytes, monocytes, etc.). Other components separated from the whole blood, such as red blood cells (RBCs), plasma, and/or platelets may be returned to the blood source or collected in pre-attached containers of the blood processing set.

The separated target cell population, e.g., mononuclear cells, may then be treated and irradiated in treatment component 20. As discussed above, treatment of mononuclear cells may involve the photoactivation of a photoactive agent that has been combined with the mononuclear cells. Mononuclear cell collection, harvest, and transfer using a device such as the Amicus® are described in greater detail in U.S. Pat. No. 6,027,657, the contents of which are incorporated by reference herein in its entirety. Preferably, the apparatus used for the harvesting, collection and reinfusion of mononuclear cells may be a "multifunctional" automated apheresis device, as is the case with the Amicus® Separator. In other words, the separation component 10 may be a multifunctional automated apparatus that can perform various collection protocols and/or serve multiple purposes, as may be needed by a particular hospital or facility, such that it can be used not only in the systems and methods for performing photopheresis treatment of MNC as described herein, but can also be used for other purposes including the collection of blood and blood components including platelets, plasma, red blood cells, granulocytes and/or perform plasma/RBC exchange, among other functions required by the hospital or medical facility.

Figure 3:
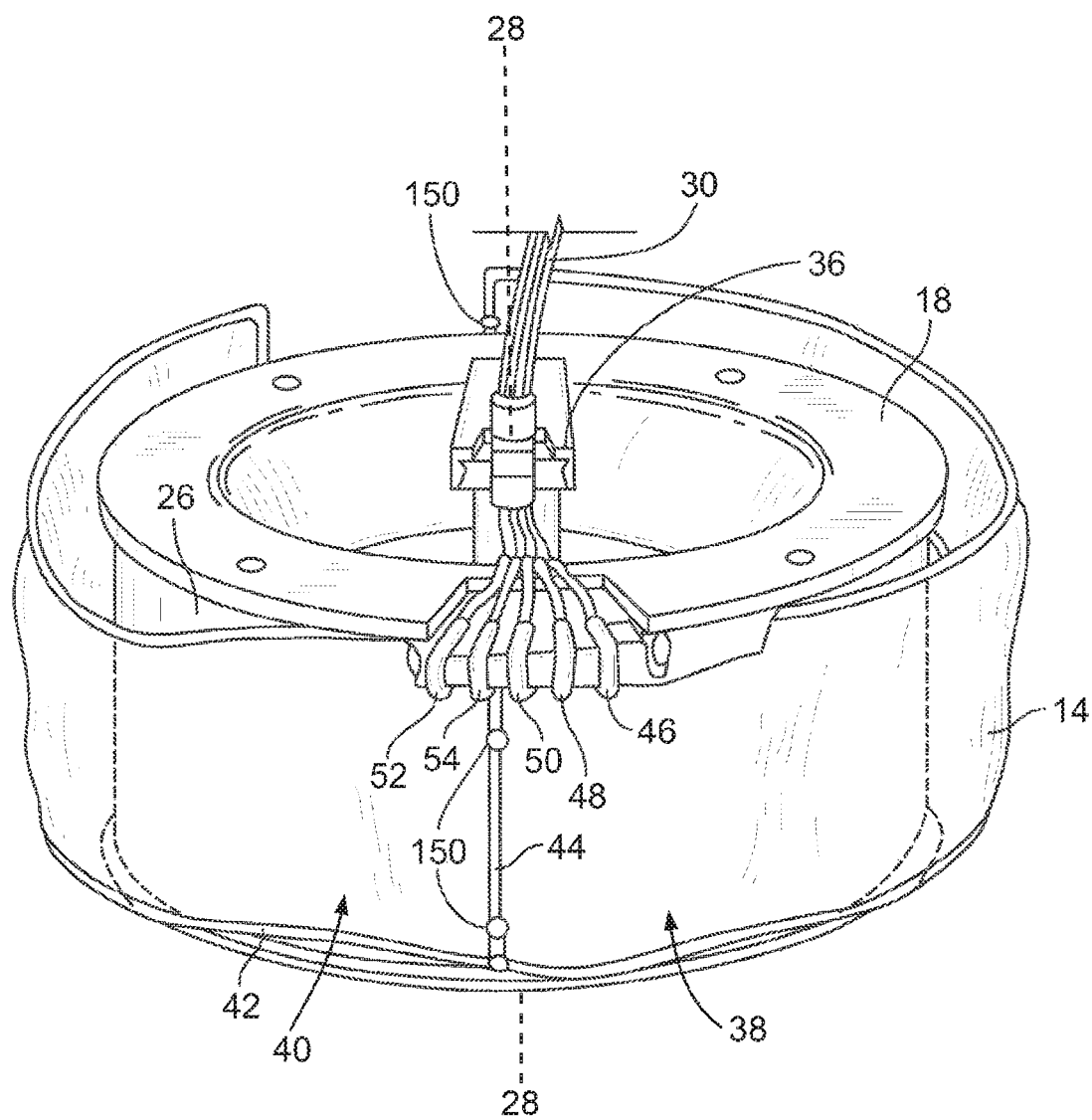
FIG. 3 is a perspective view of a separation chamber of the processing set used with the separator of FIG. 2, according to an exemplary embodiment.

FIGS. 2-4 depict a separator 10 with fluid circuit 200 mounted thereon (FIG. 2), the fluid circuit (FIG. 4) having a blood processing container 14 (FIG. 3) defining a separation chamber 12 suitable for harvesting mononuclear cells (MNC) from whole blood. As shown in FIG. 2, a disposable processing set or fluid circuit 200 (which includes container 14) may be mounted on the front panel of separator 10. The fluid circuit 200 may include a plurality of processing cassettes 23L, 23M and 23R with tubing loops for association with peristaltic pumps on separator 10. Fluid circuit 200 may also include a network of tubing and pre-connected containers for establishing flow communication with the blood source and for processing and collecting fluids and blood and blood components, as shown in FIG. 4. As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and the illumination container 68 may be pre-attached to and integral with the disposable set 200. Alternatively, container 68 may be attached to set 200 by known sterile connection techniques, such as sterile docking or the like. In FIG. 2, container 68 is shown as suspended from device 10. However, container 68 may be housed within an adjacent separately housed irradiation device 20 (as shown by broken lines in FIG. 4), thereby eliminating the step of having the operator place container 68 into irradiation device 20. The tubing leading to and/or from container 68 in fluid circuit 200 may be of a sufficient length to reach an irradiation device 20 that is adjacent to but housed separately from the separation device.

With reference to FIG. 4, fluid circuit 200 may include inlet line 72, an anticoagulant (AC) line 74 for delivering AC from container 60, an RBC line 76 for conveying red blood cells from chamber 12 of container 14 to container 67, a platelet poor plasma (PPP) line 78 for conveying PPP to container 66 and line 80 for conveying mononuclear cells to and from blood processing container 14 and collection/illumination container 68. The blood processing set may include one or more access devices (e.g., port, needle, cannula, adapter, connector, etc.) for accessing the blood source (e.g., circulatory system of a patient, blood-filled bag). As shown in FIG. 4, fluid circuit 200 may include inlet access device 70 and return access device 82. In an alternative embodiment, a single access device may serve as both the inlet and outlet access device.

Fluid flow through fluid circuit 200 may be driven, controlled and adjusted by a microprocessor-based controller in cooperation with the valves, pumps, weight scales and sensors of device 10 and fluid circuit 200, the details of which are described in the aforementioned U.S. Pat. No. 6,027,657, although any suitable controller may be used.

In accordance with the present disclosure, the fluid circuit may be further adapted for association with the irradiation device 20. One example of a suitable irradiation device is described in U.S. Pat. No. 7,433,030, which is incorporated by reference herein in its entirety, although any suitable irradiation device may be used. The irradiation device 20 may include a tray or other holder for receiving one or more containers during treatment.

Referring to FIG. 3, separation chamber 12 is defined by the walls of a flexible processing container 14 carried within an annular gap defined by a rotating spool element 18 and an outer bowl element (not shown). The blood processing container 14 may take the form of an elongated tube which is wrapped about the spool element 18 before use. The bowl and spool element 18 may be pivoted on a yoke between an upright position and a suspended position. In operation, the centrifuge 10 may rotate the suspended bowl and spool element 18 about an axis 28, creating a centrifugal field within the processing container 14. Details of the mechanism for causing relative movement of the spool 18 and bowl elements as described are disclosed in U.S. Pat. No. 5,360,542 entitled "Centrifuge with Separable Bowl and Spool Elements Providing Access to the Separation Chamber," which is also incorporated herein by reference in its entirety, although any suitable separation mechanism may be used.

Figure 5:
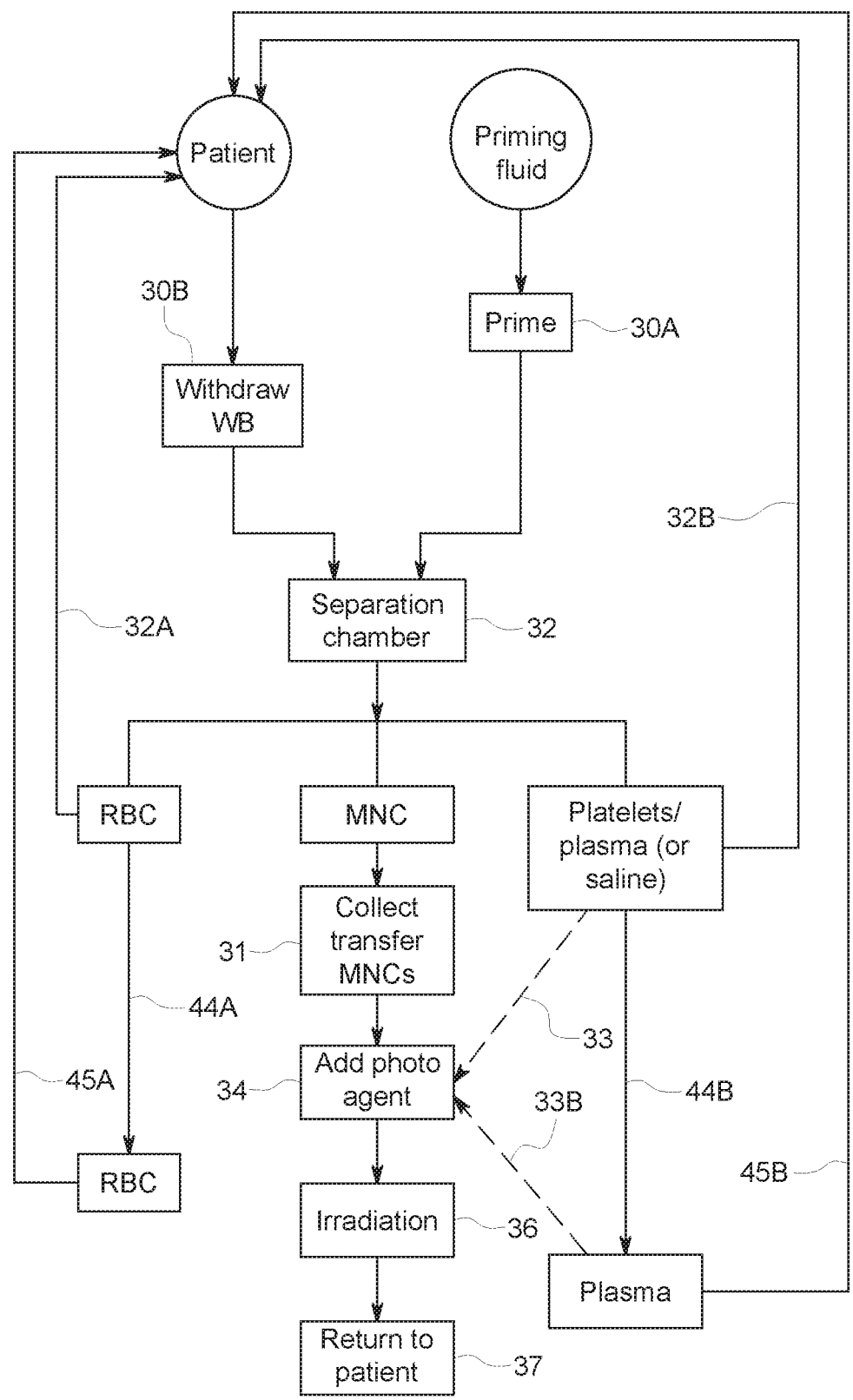
FIG. 5 is a flow chart setting forth steps of a method of an online photopheresis treatment, according to an exemplary embodiment.

FIG. 5 depicts one embodiment of an online method of treating mononuclear cells. An "online" photopheresis system includes both the blood separation device and the irradiation device in an integrated system. An online system provides for reinfusion of treated target cells back to the blood source. The fluid circuit 200 of FIG. 4 may first be primed with a priming fluid, such as saline, albumin, and/or blood components (step 30A). Whole blood may then be withdrawn from a blood source (step 30B) through inlet access device 70 (FIG. 4) and introduced into the separation chamber 12 of container 14 of processing set 200, where the whole blood is subjected to a centrifugal field. The centrifugal field may separate the target cell population, e.g., mononuclear cells, from a red blood cell constituent and a platelet/plasma constituent (step 32). A portion of the components of red blood cells and platelets/plasma may be returned to the blood source (steps 32A and 32B). Another portion of red blood cells and platelets/plasma may be diverted to other portions of the fluid circuit 200 (e.g., container 67 for RBCs, container 66 for plasma/platelets) for further utilization and/or processing (steps 44A and 44B). Collection of the mononuclear cells may proceed in one or more cycles comprising steps 30B, 32, 32A, 32B, 33B, 44A, and 44B, with the number of processing cycles conducted in a given therapeutic procedure depending upon the total yield of MNCs to be collected. During collection of the MNCs over one or more cycles, anticoagulated whole blood may enter the separation chamber 12 continuously, at select intervals, and/or for a predetermined period of time. Once the desired number of cycles has taken place, the MNCs accumulated in the separation chamber 12 may be collected (step 31). A photoactivation agent may be added to the collected MNCs (step 34), and the MNCs may be irradiated (step 36). The portion of red blood cells and platelets/plasma that were diverted to other portions of the fluid circuit 200 in steps 44A and 44B may be reinfused into the blood source (steps 45A and 45B) while the MNCs are being irradiated in step 36, or they may be reinfused during reinfusion of the irradiated MNCs into the blood source (step 37).

Although FIG. 5 depicts an online method of treating MNCs, offline methods are available as well. In offline methods, an apheresis device may be used to collect target cells. The collected target cells, typically contained in one or more collection containers, are severed or otherwise separated from the tubing set used during collection, where they are later treated in a separate irradiation or UVA light device followed by subsequent reinfusion of the treated cells to a blood source. During such offline methods, when the cells are transferred from the apheresis device to the irradiation device (which device may be located in another room or laboratory), communication with the blood source is severed and the cells detached from the blood source.

Effective treatment of the MNCs with light may be facilitated by collecting mononuclear cells in a suspension having a suitable hematocrit, volume, and/or thickness. The hematocrit, volume, and/or thickness of the MNC suspension to be treated may affect the amount of UV light absorbed by the MNCs, given that the red blood cells in the MNC suspension block at least a portion the UV light from reaching the targeted MNCs. Control of hematocrit may be desirable in cases in which the light source of the irradiation device is configured to irradiate a set intensity of light, limited settings of light intensity values, and/or a set dose of irradiation, although hematocrit/thickness control may be desirable also in cases in which intensity, dose, and/or exposure settings may readily be adjusted according to hematocrit. It is common for a transmitter (e.g., bank of light bulbs) of an irradiation device to not be adjustable in terms of intensity of emission and therefore may emit a near-constant intensity of light. If the hematocrit of the suspended MNCs is too high (such that the red blood cells prevent the absorption of light by the MNCs), it may be desired to dilute the mononuclear cells with a diluting solution, such as plasma or saline, as shown in step 33 (FIG. 5), to control the hematocrit, volume, and/or thickness so that a desired amount of UV light will reach the targeted MNC. The diluted mononuclear cells (in container 68) may then be combined with the suitable photoactivation agent in step 34.

A procedure may often involve introducing fluids into the fluid circuit in excess of the optimal fluid volume to be reinfused into the blood source. For example, saline may be introduced into the fluid circuit 200 (FIG. 4) at the initial priming stage (e.g., step 30A of FIG. 5). Saline may also be added to the MNC suspension (e.g., steps 33 and/or 33B). Anticoagulant may be added to source blood during the draw process (e.g., step 30B of FIG. 5). Reinfusing treated cells and fluid remaining in the fluid circuit may result in a blood source's fluid balance at the end of the procedure being positive compared to the initial blood volume prior to the procedure. For certain blood sources for which even small total fluid volume changes (both positive and negative) are undesirable, e.g., lung transplant patients, products intended for lung transplant patients, low blood volume patients, products intended for low blood volume patients, etc., it may be desirable to monitor the final fluid balance and adjust the procedure to maintain a close to constant total blood volume before and after the procedure.

Some embodiments may allow an operator to input a target fluid balance of a blood source (e.g., donor, patient, blood-filled container, etc.) and adjust a fluid procedure accordingly.

Some embodiments may adjust a fluid procedure during the procedure based on a blood source becoming hypervolemic due to anticoagulation, saline boluses, prime fluid, saline drip, and/or reinfusion.

Some embodiments may provide an estimate of the final fluid balance of a blood source (e.g., donor, patient, container, etc.) and make necessary procedural changes to keep the blood source at a desired fluid balance.

Table 1 shows a number of inputs an operator may enter into the system 5 of FIG. 1 that may be used by the controller to monitor fluid balance and adjust the procedure. The inputs may comprise default settings that may be optionally changed by an operator, settings that may be hard-coded into the system, and/or open settings intended to be manually inputted by an operator.

Based on one or more of the inputted information in Table 1, an estimate of the final fluid balance of a blood source may be calculated. In an embodiment in which TBV is calculated based on patient parameters, the controller may be configured to calculate TBV according to Equations 1a and 1 b, where patient weight W is in kg and patient height H is in meters:

$$TBV_{female}=(0.3561H^3+0.03308W+0.1833)\times 1000 \quad \{\text{Eq. 1a}\}$$

$$TBV_{male}=(0.3669H^3+0.03219W+0.6041)\times 1000 \quad \{\text{Eq. 1b}\}$$

Based on the citrate infusion rate (CIR), the ACD Ratio, and the weight of the patient, the controller may be configured to calculate an acceptable whole blood flow rate for step 30B of FIG. 5 according to Equations 2a and 2b, where CIR is in mg/kg/min, weight W is in kg, and using an example in which the anticoagulant solution used has a citrate ion concentration of 21.4 mg/mL:

TABLE 1

| Input name | Description |
| --- | --- |
| ACD Ratio | Configured ratio (e.g., in volume) of extracorporeal unanticoagulated whole blood to anticoagulant during step 30B of FIG. 5. For example, a 10:1 ACD volume ratio is equal to 10 units in volume of extracorporeal unanticoagulated whole blood processed to 1 unit of anticoagulant. |
| Citrate Infusion Rate (CIR) | Configured rate of citrate infusion into the system during step 30B of FIG. 5 based on the citrate concentration of the anticoagulant solution and a threshold determined by operator of mass of citrate per body weight per time. For example, it may be determined that a threshold CIR is 1.25 mg of citrate per kg of body weight per minute (1.25 mg/kg/min). |
| Plasma Flush per Cycle | Configured volume of plasma used in step 33B of FIG. 5 to gather any remaining MNCs into container 68 of FIG. 4 |
| Patient Parameters | Gender, height, weight, and hematocrit of the blood source prior to step 30B of FIG. 5. Hematocrit may be obtained, e.g., by historical patient information or sampling the whole blood prior to the procedure. |
| WB to Process (WBP) | Configured volume of total whole blood to process during the procedure. Default value may be, e.g., 2 liters. Operator may manually edit WB to process, e.g., based on the total amount of MNCs desired. |
| Custom Prime (Custom Prime HCT) | If custom prime is selected, the fluid circuit may be primed with fluid in addition to saline during step 30A. For example, for low blood volume patients, an operator may choose to prime the circuit first with saline prior to connecting with the patient. After connecting with the patient, albumin or blood components may be used to displace the saline in the fluid circuit while diverting the saline away from the patient so that the patient receives blood as the patient's own blood is being drawn out in step 30b of FIG. 5. An operator may input the hematocrit of the custom prime fluid. If custom prime is not selected, regular prime with saline without custom prime fluid may be performed. |
| Divert Prime | If divert prime is selected, prime fluid leaving the separation chamber 12 of FIG. 4 may be diverted to a separate container, e.g., container 66 of FIG. 4, rather than returning to the blood source. If divert prime is not selected, prime fluid may return to the blood source, via step 32B of FIG. 5. |
| Reinfusion | An operator may choose from a number of reinfusion options for steps 45A, 45B, and 37 of FIG. 5. For example, both treated cells and blood components remaining in the fluid circuit may be reinfused in steps 45A, 45B, and 37. In another example, only treated cells may be reinfused in step 37. In yet another example, only blood components remaining in the fluid circuit may be reinfused in steps 45A and 45B. |
| Total Blood Volume (TBV) | Total blood volume of the blood source may be manually inputted or may be calculated based on the other inputted information. Total blood volume may be updated within the system throughout the procedure. |
| MNC Transfer Rate | Configured flow rate during step 31 of FIG. 5 of MNCs being directed from the separation chamber 12 of FIG. 4 to container 68. The MNC transfer rate may be set at a default setting, e.g., 10 mL/min. |
| PRP Flush Rate | Configured flow rate during step 45B of FIG. 5 during which platelet-rich plasma that has settled towards the bottom of container 66 of FIG. 4 may be returned to the blood source via the separation chamber 12. The PRP flush rate may be set at a default setting, e.g., 45 mL/min. |
| Plasma Flush Volume | Configured volume during step 33B of FIG. 5 during which a portion of platelet-poor plasma in container 66 of FIG. 4 may be directed to container 68 to dilute MNCs. The plasma flush volume may be set at a default setting. |
| PRP Rate | Calculated flow rate during step 33B of FIG. 5 during which the plasma flush volume in container 66 of FIG. 4 is directed to container 68 to dilute MNCs. The PRP rate may be calculated based on patient parameters. |

$$EqQb = \frac{CIR \times (ACD \text{ Ratio} + 1) \times W}{21.4 \text{ mg/mL}} \quad \{\text{Eq. 2a}\}$$

WB Flow Rate = {Eq. 2b}
max(min(EqQb, Maximum WB Flow Rate), 10)

EqQb derived from equation 2a refers to how high the WB Flow Rate may be set to ensure that the CIR stays within the programmed limit (e.g., CIR set to 1.25 mg/kg/min). Equation 2b shows that WB Flow Rate may not exceed a maximum WB flow rate. WB Flow Rate may also not exceed EqQb, and the lower value between the maximum WB Flow Rate and the EqQb will be selected. A minimum WB Flow Rate may be utilized to maintain a certain level of accuracy around the volume pumped, and the system may be configured with a minimum WB Flow Rate of 10. In such a case, the controller may be configured to select as the WB Flow Rate the higher value between 10 mL/min and the lower value between EqQb and the maximum WB flow rate. In one embodiment, the system 5 may be configured to have a maximum WB flow rate of 80 mL/min. In the event the WB flow rate is less than ACD Ratio plus 1, the system may be configured to alert an operator that the ACD ratio is unachievable. Equations 2a and 2b may be used to determine flow rate at step 30B except when MNCs are transferred to collection container 68 of FIG. 4 in step 31 of FIG. 5. During step 31, a different equation (equation 7a below) may be used to determine step 30B.

Based on WB Flow Rate calculated from Equation 2b and Whole Blood to Process (WBP) listed in Table 1, the controller may be configured to calculate Collection Time, which may be characterized as the time it takes to collect MNCs within separation chamber 12 of FIG. 4 from the total whole blood to process, where WB to Process is in mL and WB Flow Rate is in mL/min:

$$\text{Collection Time} = \frac{WB \text{ to Process}}{WB \text{ Flow Rate}} \quad \{\text{Eq. 3}\}$$

Based on WBP and the ACD Ratio in Table 1, the volume of anticoagulant solution required at step 30B of FIG. 5 during collection of MNCs in the separation chamber may be calculated. The anticoagulant solution volume required may be calculated by Equation 4, where WBP is in mL:

$$AC \text{ Vol. Required During Collection} = \frac{WB \text{ to Process}}{ACD \text{ Ratio} + 1} \quad \{\text{Eq. 4}\}$$

Based on the ACD Ratio, the blood source hematocrit expressed as a decimal, and the plasma flush per cycle (mL) from Table 1 and based on the AC Volume Required During Collection from Equation 4, the controller may calculate by Equation 5a below an estimated volume of AC that the blood source will receive by the end of the procedure, with the exception of the volume of AC contributed to the system during step 31 of FIG. 5 of MNC transfer. The result of Equation 5a may be used in Equation 5b to estimate the actual citrate infusion rate the blood source will receive, with the exception of the CIR contributed to the system during step 31 of MNC transfer.

Est. AC Vol. to Blood Source = {Eq. 5a}
$$(\text{Eq. 4}) - \frac{2 \times (\text{Plasma Flush per Cycle})}{ACD \text{ Ratio} - \frac{(HCT) \times (ACD \text{ Ratio})^2}{(ACD \text{ Ratio}) + 1} + 1}$$

$$\text{Est. Actual } CIR = \frac{(\text{Eq. 5a}) \times 21.4 \text{ mg/mL}}{\text{Weight} \times \text{Collection Time}} \quad \{\text{Eq. 5b}\}$$

Utilizing the previous equations, an estimate of the maximum extracorporeal volume of red blood cells at any given time during the procedure (Max RBC Out) may be calculated based on knowledge of the areas of the fluid circuit where the red blood cells are known to reside during the procedure. The procedure may be known to have the Max RBC Out during step 44A of FIG. 5 when a portion of red blood cells may be diverted to other portions of the fluid circuit 200, e.g., into container 67 (FIG. 4). The controller may be configured to display to an operator this estimate of the maximum extracorporeal volume of red blood cells. The Max RBC Out may be expressed as a percentage of a blood source's total RBCs in circulation within the system 5 (FIG. 1), including the blood source. In one embodiment, the system may be configured to provide a response action when Max RBC Out is greater than 10-15%. Equation 6a may be used to determine the hematocrit of anticoagulated whole blood (Hct AC WB) prior to separation, using the ACD Ratio and the blood source hematocrit value expressed as a decimal. The Max RBC Out may be calculated using Equations 6b and 6c. Equation 6b may be used for an embodiment in which custom prime has not been selected, and Equation 6c may be used for an embodiment in which custom prime has been selected.

$$Hct \text{ } AC \text{ } WB = \frac{HCT \times ACD \text{ Ratio}}{ACD \text{ Ratio} + 1} \quad \{\text{Eq. 6a}\}$$

$$\text{Max } RBC \text{ Out} = \frac{(130.46 \times Hct \text{ } ACWB) + 0.85(45.89 + RBC \text{ Chamber})}{TBV \times Hct \text{ } ACWB} \quad \{\text{Eq. 6b}\}$$

$$\text{Max } RBC \text{ Out} = \frac{(130.46 \times Hct \text{ } ACWB) + 0.85(45.89 + RBC \text{ Chamber})}{(139.36 \times \text{Custom Prime } HCT) + (TBV \times Hct \text{ } ACWB)} \quad \{\text{Eq. 6c}\}$$

HCT ACWB in equation 6a refers to the hematocrit of anticoagulated whole blood within the whole blood fluid flow path of the fluid circuit 200 FIG. 4. In one embodiment, the whole blood fluid flow path may comprise the path from the access device 72 to the left cassette 23L to the separation chamber 12. 130.46 mL in equation 6b represents the fluid volume capacity of the whole blood fluid flow path between the access device 72 and the separation chamber 12, although a different number may be used in the equation for a different whole blood fluid flow path (e.g., different fluid circuit, different pathway configuration, etc.). RBC Chamber in equation 6b refers to the volume (in mL) of cells (primarily RBCs) pumped from the separation chamber 12 of FIG. 4 during step 44A of FIG. 5. RBC Chamber may be pre-configured as a default setting within the system or may be inputted by an operator. In one embodiment, the packed RBC flow path of the fluid circuit 200 may comprise the path from the separation chamber 12 to the middle cassette 23M to the RBC container 67. 45.89 mL in equation 6b represents the fluid volume capacity of the RBC fluid flow path, including the volume of RBCs disposed in container 67. Equation 6b uses 0.85 as the estimate for the hematocrit of the packed RBCs disposed within the separation chamber 12 and the RBC fluid pathway. Equation 6c is similar to Equation 6b, except Equation 6b takes into account the custom prime fluid that has been placed into circulation within the fluid circuit. The RBCs contributed by the custom prime fluid may be described as the Custom Prime HCT (Table 1) (expressed as a decimal) multiplied by the fluid volume capacity (e.g., 139.36 mL) of the custom prime fluid flow path. In one embodiment, the custom prime fluid flow path may comprise the pathway from the access device 72, into the left cassette 23L, into the centrifuge, into the middle cassette 23M, into the left cassette 23L, and back to the blood source via access device 82.

As mentioned previously, equations 2a through 5b did not account for fluid volume contributions made during MNC transfer (step 31 of FIG. 5) during which MNCs collected within the separation chamber 12 of FIG. 4 are transferred to the container 68. During MNC transfer, the whole blood flow rate during step 30B may be calculated by equation 7a as WB Flow Rate Transfer (WBFRT), which is a function of the ACD Ratio from Table 1 and the WB Flow Rate from equation 2b:

$$\text{WBFRT}=\max(\min(\text{ACD Ratio}+1,\text{WB Flow Rate}), 10) \quad \{\text{Eq. 7a}\}$$

From the WBFRT, the volume of fluid used to push the MNCs out of the separation chamber 12 may be calculated by equation 7b. During step 31 of FIG. 5, RBC Chamber in equation 7b may comprise the same numerical value as RBC Chamber from equations 6b and 6c, but the volume for RBC Chamber in equation 7b may include both RBCs and MNCs. Additionally, 30 mL of RBCs from container 67 of FIG. 4 may be used to push the MNCs within the volume represented by RBC Chamber and is included in equation 7b.

$$\text{Transfer Volume}=30+\text{RBC Chamber} \quad \{\text{Eq. 7b}\}$$

From the WBFRT of equation 7a, the Transfer Volume from equation 7b, and the MNC Transfer Rate, PRP Flush Rate, PRP Flush Volume, and the PRP Rate from Table 1, Equation 7c may be used to calculate the Whole Blood to Process during the transfer step of 31 of FIG. 5.

$$WBP\text{ Transfer}=WBFRT\times\left(\frac{\text{Transfer Volume}}{MNC\text{ Transfer Rate}}+\frac{\text{Transfer Volume}}{PRP\text{ Flush Rate}}+\frac{\text{Plasma Flush Volume}}{PRP\text{ Rate}}\right) \quad \{\text{Eq. 7c}\}$$

From the WBP Transfer value from equation 7c and the ACD Ratio, equation 7d may be used to calculate the anticoagulant volume required during the transfer step of 31 of FIG. 5.

$$AC\text{ Required Transfer}=\frac{WBP\text{ Transfer}}{ACD\text{ Ratio}+1} \quad \{\text{Eq. 7d}\}$$

Knowing the anticoagulant volume required during transfer from equation 7d and the anticoagulant required during collection from equation 4, the total anticoagulant required for the whole procedure may be calculated by equation 8. AC Required Transfer may be multiplied in equation 8 by the number of transfer cycles performed. In one embodiment, the number of transfer cycles may be set to 2.

$$\text{Total AC Required}=\text{AC Vol. Required During Collection}+2(\text{AC Required Transfer}) \quad \{\text{Eq. 8}\}$$

Once the Total AC Required is known, an estimated net change in volume by the end of the procedure may be calculated based on the inputs of Table 1 and equations 9a through 9c below. Equation 9a may be used for the net change in blood volume in an embodiment in which the blood components remaining in the fluid circuit may be reinfused to the blood source along with treated cells during step 37.

$$\Delta\text{Blood Volume}=180\text{ mL}+\text{Total AC Required}+160\text{ mL} \quad \{\text{Eq. 9a}\}$$

180 mL in equation 9a refers to the volume of a diluting solution (e.g., saline) not originally from the blood source that may have been used in step 33 of FIG. 5 to dilute the MNCs in container 68 of FIG. 4. If plasma from the blood source or other blood component from the blood source is used as the diluting solution, this volume may be removed from equation 9a. 160 mL in equation 9a refers to an example volume of saline that may have entered the fluid circuit in the course of the procedure, e.g., from container 64 of FIG. 4. Saline may have contributed to the 160 mL during the priming process, in the course of administering a saline drip (if the blood source is a patient that requires vein access to be open), etc.

In an embodiment in which prime fluid leaving the separation chamber 12 of FIG. 4 is diverted to a separate container instead of returning to the blood source as shown in step 32B of FIG. 5, Equation 9b may be used for the net change in blood volume to exclude the diverted volume from the equation.

$$\Delta\text{Blood Volume}=180\text{ mL}-90\text{ mL}+\text{Total AC Required}+160\text{ mL} \quad \{\text{Eq. 9b}\}$$

90 mL in equation 9b represents an example volume of prime fluid diverted into the separate container.

Equation 9c may be used for the net change in blood volume in an embodiment in which only the treated cells in container 68 of FIG. 4 are reinfused to the blood source during step 37 without reinfusing the blood components remaining in the fluid circuit.

$$\Delta\text{Blood Volume}=180\text{ mL}+\text{Total AC Required}+25\text{ mL} \quad \{\text{Eq. 9c}\}$$

25 mL in equation 9a represents an example volume of fluid not originating from the blood source (e.g., saline) that may be used during reinfusion of the treated cells in container 68 of FIG. 4 back to the blood source. For example, after most of the treated cells have been returned to the blood source, 25 mL of saline may be used to rinse and recover any remaining treated cells in the fluid flow path between container 68 and the blood source. In an embodiment in which prime fluid is diverted, the volume of prime fluid diverted may be subtracted from the result of equation 9c.

Once the estimated net change in volume by the end of the procedure from equation 9a, 9b, or 9c is known, an estimated fluid balance expressed as a multiple of TBV (equation 1a or 1b) may be determined according to equation 10.

$$\text{Fluid Balance}=1+\frac{\Delta\text{ Blood Volume}}{TBV} \quad \{\text{Eq. 10}\}$$

The controller may be programmed with minimum and maximum limits for fluid balance. In one embodiment, the controller may be configured to have a permissible fluid balance in the range of 0.95 to 1.3. In the event the fluid balance is outside the programmed range, the controller may be configured to perform a response action, which may comprise allowing automatic or manual changes to procedure parameters that affect fluid balance.

The system and controller may be programmed to allow an operator to make changes or implement automatic changes to a fluid procedure based on the estimated fluid balance derived from equation 10. One or more changes may be implemented in order to lower or raise the fluid balance to a desired value or range. In an embodiment in which the priming phase of step 30A of FIG. 5 has not yet reached completion, the change may comprise changing settings for the diversion of prime fluid (referring to equations 9a through 9c). If it desired to lower the fluid balance and prime fluid is not set to be diverted, prime fluid diversion may be selected. If it is desired to raise the fluid balance and prime fluid is set to be diverted, prime diversion may be turned off.

In an embodiment in which the priming phase of step 30A of FIG. 5 has not begun, the change may comprise changing the anticoagulant solution to one having a different AC citrate concentration (referring to equation 2a). If it is desired to lower the fluid balance, an anticoagulant solution having an increased AC citrate concentration may be selected. If it is desired to raise the fluid balance, an anticoagulant solution having a decreased AC citrate concentration may be selected.

In another embodiment, at any point in the procedure, the change may comprise changing the ACD ratio setting (primarily determined by equations 4 and 7d). If it is desired to lower the fluid balance, the ACD ratio may be raised. If it is desired to raise the fluid balance, the ACD ratio may be lowered.

In another embodiment, at any point in the procedure, the change may comprise altering the value for WB to process (referring to equations 4 and 8). If it is desired to lower the fluid balance, the WBP may be lowered to decrease the amount of citrate returning to the blood source. If it is desired to raise the fluid balance, the WBP value may be raised to increase the amount of citrate returning to the blood source.

In another embodiment, at any point in the procedure, the change may comprise altering settings for reinfusing treated cells and/or blood components remaining in the fluid circuit (referring to equations 9a and 9c). If it is desired to lower the fluid balance, an operator may elect to reinfuse back to the blood source the treated cells without returning blood components remaining in the fluid circuit (equation 9c). Otherwise, in some instances, an operator may elect to reinfuse back to the blood source blood components remaining in the fluid circuit without returning the treated cells. If it is desired to raise the fluid balance, an operator may elect to reinfuse back to the blood source both the treated cells and blood components remaining in the fluid circuit (equation 9a).

In another embodiment, at any point in the procedure, the change may comprise altering the value for RBC Chamber (referring to equation 7b). If it is desired to lower the fluid balance, the RBC Chamber may be lowered to decrease the anticoagulant required during MNC Transfer (equation 7d). If it is desired to raise the fluid balance, the RBC Chamber may be raised to increase the anticoagulant required during MNC Transfer.

In another embodiment, at any point in the procedure, the change may comprise concentrating the treated cells prior to returning to the blood source in step 37 of FIG. 5 by directing the treated cells from container 68 of FIG. 4 after treatment into the separation chamber 12 to separate the treated cells from the diluent (e.g., saline, plasma) before returning the concentrated treated cells to the blood source.

In an embodiment in which the estimate of the maximum extracorporeal volume of red blood cells (Max RBC Out in equations 6b and 6c) is above a threshold, the system may be configured to automatically or manually lower the RBC Chamber value (equations 6b and 6c) until Max RBC Out reaches a threshold. The system may also be configured to switch priming fluid from saline during step 30A of FIG. 5 to prime fluid having a positive hematocrit (triggering equation 6c) so that the blood source receives blood as whole blood is being drawn out in step 30B.

Without limiting the foregoing description, in accordance with one aspect of the subject matter herein, there is provided a system for monitoring and controlling fluid balance during an extracorporeal photopheresis procedure. The system comprises a disposable fluid circuit comprising a product container configured to receive a target cell component. The system also comprises a separator configured to work in association with the disposable fluid circuit, the separator comprising a chamber configured to rotate about a rotational axis and convey whole blood from a blood source into an inlet region of the chamber for separation into a red blood cell component, a plasma component, and the target cell component. The system also comprises a microprocessor-based controller in communication with the separator. The controller is configured to estimate an end-of-procedure fluid balance by calculating a total volume of anticoagulant solution having a citrate concentration to be used for the procedure, wherein the end-of-procedure fluid balance is estimated based on manual or automatic inputs comprising an ACD ratio relating unanticoagulated extracorporeal whole blood to anticoagulant solution, an amount of whole blood to process, a citrate infusion threshold rate, a patient body weight associated with the blood source, and a total blood volume of the blood source. The controller is also configured to draw anticoagulated whole blood into the disposable fluid circuit and the chamber at a whole blood flow rate. The controller is also configured to separate the anticoagulated whole blood into the red blood cell component, the target cell component, and the plasma component. The controller is also configured to direct the target cell component to the product container, treat the product container comprising the target cell component to create a treated target cell component, and return to the blood source the treated target cell component, a portion of the red blood cell component remaining in the fluid circuit, and/or a portion of the plasma component remaining in the fluid circuit. The controller is also configured to provide a first response action if the end-of-procedure fluid balance estimated is above or below a programmed fluid balance range.

In accordance with a second aspect which may be used or combined with the immediately preceding aspect, the controller is further configured to calculate the total volume of the blood source with information comprising a gender, height, and weight of the blood source.

In accordance with a third aspect which may be used or combined with any of the preceding aspects, a maximum extracorporeal volume of red blood cells during the procedure is estimated based on the ACD ratio, a hematocrit of the blood source, a hematocrit of a priming fluid, and the total blood volume. A second response action is provided if the estimated maximum extracorporeal volume of red blood cells is above or below a programmed limit.

In accordance with a fourth aspect which may be used or combined with any of the preceding aspects, the end-ofprocedure fluid balance is further estimated based on a volume of fluid not returning to the blood source, and the first response action comprises at least one of altering the volume of fluid not returning to the blood source, changing the citrate concentration of the anticoagulant solution, changing the ACD ratio, changing the amount of whole blood to process, altering settings for components returned to the blood source, and concentrating the treated target cell component in the separator prior to returning the treated target cell component to the blood source.

In accordance with a fifth aspect which may be used or combined with any of the preceding aspects, the controller is further configured to calculate the total volume of anticoagulant solution to be used for the procedure based on the whole blood flow rate calculated based on manual or automatic inputs comprising the ACD ratio, the citrate infusion threshold rate, and the patient body weight associated with the blood source.

In accordance with a sixth aspect which may be used or combined with any of the preceding aspects, the target cell component comprises mononuclear cells, and the treated target cell component comprises mononuclear cells combined with a photoactivation agent and subjected to irradiation.

In accordance with a seventh aspect which may be used or combined with any of the preceding aspects, the programmed fluid balance range is 0.95 to 1.30.

In accordance with an eighth aspect which may be used or combined with the third aspect, the second response action comprises changing the priming fluid to a priming fluid having a higher hematocrit.

In accordance with a ninth aspect which may be used or combined with any of the third or eighth aspects, the programmed limit is 10-15% of a total amount of red blood cells of the blood source.

In accordance with a tenth aspect, there is provided a method for monitoring and controlling fluid volume balance during an extracorporeal photopheresis procedure, driven and adjusted by a microprocessor-based controller. The controller is configured manually or automatically with a first set of inputs comprising a hematocrit of a blood source, a total blood volume of the blood source, and an ACD ratio relating unanticoagulated extracorporeal whole blood to anticoagulant solution. A maximum extracorporeal red blood cell amount during the procedure is estimated based on the first set of inputs. A fluid circuit is primed with a priming fluid having a prime fluid hematocrit value inputted into the controller. Whole blood is drawn from the blood source into the fluid circuit and a separator. The whole blood is separated into a red blood cell component, a target cell component, and a plasma component. The target cell component is directed to a product container. The product container comprising the target cell component is treated to create a treated target cell component. The treated target cell component, a portion of the red blood cell component remaining in the fluid circuit, and/or a portion of the plasma component remaining in the fluid circuit is returned to the blood source. A first response action is provided if the maximum extracorporeal red blood cell amount estimated is above a programmed limit.

In accordance with an eleventh aspect which may be used or combined with the tenth aspect, the total blood volume of the blood source is calculated with information comprising a gender, height, and weight of the blood source.

In accordance with a twelfth aspect which may be used or combined with the any of the tenth or eleventh aspects, the prime fluid hematocrit value comprises a positive value, and the maximum extracorporeal red blood cell amount during the procedure is estimated based also on the positive value.

In accordance with a thirteenth aspect which may be used or combined with any of the tenth through twelfth aspects, the first response action comprises changing the priming fluid to a priming fluid having a different prime fluid hematocrit value.

In accordance with a fourteenth aspect which may be used or combined with any of the tenth through thirteenth aspects, the controller is configured manually or automatically with a second set of inputs comprising an amount of whole blood to process, a citrate infusion threshold rate, and a patient body weight associated with the blood source. An end-of-procedure fluid balance is estimated based on the second set of inputs and an input from the first set of inputs. A second response action is provided if the estimated end-of-procedure fluid balance is above or below a programmed fluid balance range.

In accordance with a fifteenth aspect which may be used or combined with any of the tenth through fourteenth aspects, the target cell component comprises mononuclear cells.

In accordance with a sixteenth aspect which may be used or combined with any of the tenth through fifteenth aspects, the treated target cell component comprises mononuclear cells combined with a photoactivation agent and subjected to irradiation.

In accordance with a seventeenth aspect which may be used or combined with the fourteenth aspect, the programmed fluid balance range is 0.95 to 1.30.

In accordance with an eighteenth aspect which may be used or combined with any of the tenth through seventeenth aspects, the programmed limit is 10-15% of a total amount of red blood cells of the blood source.

In accordance with a nineteenth aspect, there is provided a method for monitoring and controlling fluid volume balance during an extracorporeal photopheresis procedure, driven and adjusted by a microprocessor-based controller. 1) The controller is configured manually or automatically with inputs comprising a hematocrit of a blood source, a total blood volume of the blood source, an ACD ratio relating unanticoagulated extracorporeal whole blood to anticoagulant solution, a citrate infusion threshold rate, a volume of whole blood to process, and a patient body weight associated with the blood source. 2) A fluid circuit is primed with a priming fluid. 3) None or some of the priming fluid is returned to the blood source. 4) Whole blood is withdrawn from the blood source into the fluid circuit at a first flow rate and anticoagulant solution is withdrawn at a second flow rate in accordance with the ACD ratio, the citrate infusion threshold rate, the volume of whole blood to process, and the patient body weight. 5) The whole blood is separated within a separation chamber into a red blood cell component, a mononuclear cell component, and a plasma component. 6) A first portion of the red blood cell component and a first portion of the plasma component are returned to the blood source. 7) A second portion of the red blood cell component and a second portion of the plasma component are retained within the fluid circuit. 8) The mononuclear cell component is collected in the separation chamber over a plurality of cycles comprising steps 4 through 7, while anticoagulated whole blood enters the separation chamber continuously, at select intervals, and/or for a predetermined period of time. 9) A volume of fluid comprising the mononuclear cell component and a third portion of the red blood cell component is pumped from the separation chamber at an MNC transfer rate. 10) The mononuclear cell component is directed into a first container without the red blood cell component. 11) The mononuclear cell component is diluted with a volume of the second portion of the plasma component within the fluid circuit pumped into the first container at a PRP rate. 12) A photoactivation agent is added to the mononuclear cell component to create an agent-added mononuclear cell component. 13) The agent-added mononuclear cell component is irradiated to create a photoactivated mononuclear cell component. 14) The photoactivated mononuclear cell component, the second portion of the red blood cell component, and/or the second portion of the plasma component is returned. The controller is configured to estimate throughout the procedure an end-of-procedure fluid balance based on the inputs of step 1, any priming fluid returned to the blood source in step 3, the volume of fluid in step 9, the MNC transfer rate in step 9, the volume of the second portion of the plasma component within the fluid circuit in step 11, and the PRP rate in step 11. The controller is configured to provide a response action if the end-of-procedure fluid balance is above or below a programmed fluid balance range.

In accordance with a twentieth aspect which may be used or combined with the immediately preceding aspect, the response action comprises at least one of altering an amount of priming fluid returned to the blood source in step 3, changing a citrate concentration of the anticoagulant solution, changing the ACD ratio, changing the volume of whole blood to process, changing the volume of fluid in step 9, altering settings for components returned in step 14, and concentrating the photoactivated mononuclear cell component in the separation chamber prior to returning the photoactivated mononuclear cell component to the blood source.

The embodiments disclosed herein are for the purpose of providing a description of the present subject matter, and it is understood that the subject matter may be embodied in various other forms and combinations not shown in detail. For example, the subject matter may be applied to any technology in which biological fluid is combined with another fluid (e.g., apheresis, dialysis, transfusion, diagnostics, cell washing, cell therapy, infusion, anesthesia, etc.). Therefore, specific embodiments and features disclosed herein are not to be interpreted as limiting the subject matter as defined in the accompanying claims.

The invention claimed is:

1. A system for monitoring and controlling fluid balance during an extracorporeal photopheresis procedure, comprising:
    a disposable fluid circuit comprising a product container configured to receive a target cell component;
    a separator configured to work in association with the disposable fluid circuit, the separator comprising a chamber configured to rotate about a rotational axis and convey whole blood from a blood source into an inlet region of the chamber for separation into a red blood cell component, a plasma component, and the target cell component;
    a microprocessor-based controller in communication with the separator, wherein the controller is configured to:
        estimate an end-of-procedure fluid balance by calculating a total volume of anticoagulant solution having a citrate concentration to be used for the procedure, wherein the end-of-procedure fluid balance is estimated based on manual or automatic inputs comprising an ACD ratio relating unanticoagulated extracorporeal whole blood to anticoagulant solution, an amount of whole blood to process, a citrate infusion threshold rate, a patient body weight associated with the blood source, and a total blood volume of the blood source;
        draw anticoagulated whole blood into the disposable fluid circuit and the chamber at a whole blood flow rate;
        separate the anticoagulated whole blood into the red blood cell component, the target cell component, and the plasma component;
        direct the target cell component to the product container;
        treat the product container comprising the target cell component to create a treated target cell component;
        return to the blood source the treated target cell component, a portion of the red blood cell component remaining in the fluid circuit, and/or a portion of the plasma component remaining in the fluid circuit; and
        provide a first response action if the end-of-procedure fluid balance estimated is above or below a programmed fluid balance range.

2. The system of claim 1, wherein the controller is further configured to calculate the total volume of the blood source with information comprising a gender, height, and weight of the blood source.

3. The system of claim 1, wherein the controller is further configured to:
    estimate a maximum extracorporeal volume of red blood cells during the procedure based on the ACD ratio, a hematocrit of the blood source, a hematocrit of a priming fluid, and the total blood volume; and
    provide a second response action if the estimated maximum extracorporeal volume of red blood cells is above or below a programmed limit.

4. The system of claim 1, wherein the end-of-procedure fluid balance is further estimated based on a volume of fluid not returning to the blood source, and the first response action comprises at least one of altering the volume of fluid not returning to the blood source, changing the citrate concentration of the anticoagulant solution, changing the ACD ratio, changing the amount of whole blood to process, altering settings for components returned to the blood source, and concentrating the treated target cell component in the separator prior to returning the treated target cell component to the blood source.

5. The system of claim 1, wherein the controller is further configured to calculate the total volume of anticoagulant solution to be used for the procedure based on the whole blood flow rate calculated based on manual or automatic inputs comprising the ACD ratio, the citrate infusion threshold rate, and the patient body weight associated with the blood source.

6. The system of claim 1, wherein the target cell component comprises mononuclear cells, and the treated target cell component comprises mononuclear cells combined with a photoactivation agent and subjected to irradiation.

7. The system of claim 1, wherein the programmed fluid balance range is 0.95 to 1.30.

8. The system of claim 3, wherein the second response action comprises changing the priming fluid to a priming fluid having a higher hematocrit.

9. The system of claim 3, wherein the programmed limit is 10-15% of a total amount of red blood cells of the blood source.

10. A method for monitoring and controlling fluid volume balance during an extracorporeal photopheresis procedure, driven and adjusted by a microprocessor-based controller, comprising the steps of:

configuring the controller manually or automatically with a first set of inputs comprising a hematocrit of a blood source, a total blood volume of the blood source, and an ACD ratio relating unanticoagulated extracorporeal whole blood to anticoagulant solution;

estimating based on the first set of inputs a maximum extracorporeal red blood cell amount during the procedure;

priming a fluid circuit with a priming fluid having a prime fluid hematocrit value inputted into the controller;

drawing whole blood from the blood source into the fluid circuit and a separator;

separating the whole blood into a red blood cell component, a target cell component, and a plasma component;

directing the target cell component to a product container;

treating the product container comprising the target cell component to create a treated target cell component;

returning to the blood source the treated target cell component, a portion of the red blood cell component remaining in the fluid circuit, and/or a portion of the plasma component remaining in the fluid circuit; and providing a first response action if the maximum extracorporeal red blood cell amount estimated is above a programmed limit.

11. The method of claim 10, further comprising calculating the total blood volume of the blood source with information comprising a gender, height, and weight of the blood source.

12. The method of claim 10, wherein the prime fluid hematocrit value comprises a positive value, and the maximum extracorporeal red blood cell amount during the procedure is estimated based also on the positive value.

13. The method of claim 10, wherein the first response action comprises changing the priming fluid to a priming fluid having a different prime fluid hematocrit value.

14. The method of claim 10, further comprising:
configuring the controller manually or automatically with a second set of inputs comprising an amount of whole blood to process, a citrate infusion threshold rate, and a patient body weight associated with the blood source;
estimating an end-of-procedure fluid balance based on the second set of inputs and an input from the first set of inputs; and
provide a second response action if the estimated end-of-procedure fluid balance is above or below a programmed fluid balance range.

15. The method of claim 10, wherein the target cell component comprises mononuclear cells.

16. The method of claim 10, wherein the treated target cell component comprises mononuclear cells combined with a photoactivation agent and subjected to irradiation.

17. The method of claim 14, wherein the programmed fluid balance range is 0.95 to 1.30.

18. The method of claim 10, wherein the programmed limit is 10-15% of a total amount of red blood cells of the blood source.

19. A method for monitoring and controlling fluid volume balance during an extracorporeal photopheresis procedure, driven and adjusted by a microprocessor-based controller, comprising the steps of:
1) configuring the controller manually or automatically with inputs comprising a hematocrit of a blood source, a total blood volume of the blood source, an ACD ratio relating unanticoagulated extracorporeal whole blood to anticoagulant solution, a citrate infusion threshold rate, a volume of whole blood to process, and a patient body weight associated with the blood source;
2) priming a fluid circuit with a priming fluid;
3) returning none or some of the priming fluid to the blood source;
4) withdrawing whole blood from the blood source into the fluid circuit at a first flow rate and withdrawing anticoagulant solution at a second flow rate in accordance with the ACD ratio, the citrate infusion threshold rate, the volume of whole blood to process, and the patient body weight;
5) separating within a separation chamber the whole blood into a red blood cell component, a mononuclear cell component, and a plasma component;
6) returning a first portion of the red blood cell component and a first portion of the plasma component to the blood source;
7) retaining a second portion of the red blood cell component and a second portion of the plasma component within the fluid circuit;
8) collecting the mononuclear cell component in the separation chamber over a plurality of cycles comprising steps 4 through 7, while anticoagulated whole blood enters the separation chamber continuously, at select intervals, and/or for a predetermined period of time;
9) pumping a volume of fluid comprising the mononuclear cell component and a third portion of the red blood cell component from the separation chamber at an MNC transfer rate;
10) directing the mononuclear cell component into a first container without the red blood cell component;
11) diluting the mononuclear cell component with a volume of the second portion of the plasma component within the fluid circuit pumped into the first container at a PRP rate;
12) adding a photoactivation agent to the mononuclear cell component to create an agent-added mononuclear cell component;
13) irradiating the agent-added mononuclear cell component to create a photoactivated mononuclear cell component; and
14) returning the photoactivated mononuclear cell component, the second portion of the red blood cell component, and/or the second portion of the plasma component;
wherein the controller is configured to estimate throughout the procedure an end-of-procedure fluid balance based on the inputs of step 1, any priming fluid returned to the blood source in step 3, the volume of fluid in step 9, the MNC transfer rate in step 9, the volume of the second portion of the plasma component within the fluid circuit in step 11, and the PRP rate in step 11;
wherein the controller is configured to provide a response action if the end-of-procedure fluid balance is above or below a programmed fluid balance range.

20. The method of claim 19, wherein the response action comprises at least one of altering an amount of priming fluid returned to the blood source in step 3, changing a citrate concentration of the anticoagulant solution, changing the ACD ratio, changing the volume of whole blood to process, changing the volume of fluid in step 9, altering settings for components returned in step 14, and concentrating the photoactivated mononuclear cell component in the separation chamber prior to returning the photoactivated mononuclear cell component to the blood source.

* * * * *